United States Patent [19]

Buchholtz et al.

[11] Patent Number: 5,470,350
[45] Date of Patent: Nov. 28, 1995

[54] SYSTEM FOR THE TREATMENT OF PATHOLOGICAL TISSUE HAVING A CATHETER WITH A PRESSURE SENSOR

[75] Inventors: Gerhard Buchholtz, Erlangen; Ulrich Schaetzle, Roettenbach, both of Germany

[73] Assignee: Siemens Aktiengesellschaft, Munich, Germany

[21] Appl. No.: 218,582

[22] Filed: Mar. 28, 1994

[30] Foreign Application Priority Data

Apr. 2, 1993 [DE] Germany .................. 43 10 923.3

[51] Int. Cl.⁶ .................................. A61B 8/12
[52] U.S. Cl. .................. 607/97; 128/658; 128/660.03
[58] Field of Search ................ 607/96, 97, 98, 607/99, 100, 101, 102, 103, 104, 105, 113; 128/654, 656, 658, 660.01, 660.03, 660.07

[56] References Cited

U.S. PATENT DOCUMENTS

| | | |
|---|---|---|
| 4,620,546 | 11/1986 | Aida et al. . |
| 4,887,605 | 12/1989 | Angelsen et al. . |
| 4,986,275 | 1/1991 | Ishida et al. ............... 607/97 |
| 5,080,101 | 1/1992 | Dory . |
| 5,161,536 | 11/1992 | Vilkomerson et al. . |
| 5,178,148 | 1/1993 | Lacoste et al. ............ 128/660.03 |
| 5,247,935 | 9/1993 | Cline et al. ............... 607/96 |
| 5,275,165 | 1/1994 | Ettinger et al. ............. 607/96 |
| 5,304,214 | 4/1994 | DeFord et al. ............. 607/105 |
| 5,307,816 | 5/1994 | Hashimoto et al. ........ 128/660.03 |
| 5,366,490 | 11/1994 | Edwards et al. ............ 607/99 |
| 5,368,032 | 11/1994 | Cline et al. ............... 607/97 |

FOREIGN PATENT DOCUMENTS

| | | |
|---|---|---|
| 2113099 | 8/1983 | United Kingdom . |
| WO91/13650 | 9/1991 | WIPO . |

Primary Examiner—Angela D. Sykes
Assistant Examiner—Eric F. Winakur
Attorney, Agent, or Firm—Hill, Steadman & Simpson

[57] ABSTRACT

A therapy system for treating pathological tissue with heating radiation includes an ultrasound locating system and a catheter introducible into the body of a patient to be treated, the catheter having at least one pressure sensor in the region of its distal end. The catheter is used to apply the heating radiation to a specified site within the patient. The pressure sensor generates signals due to interaction with the diagnostic ultrasound waves of the ultrasound locating system, and these signals are supplied to an image generating unit within the ultrasound locating system. The image generating unit calculates the position of the pressure sensor in the ultrasound image on the basis of the signals from the pressure sensor, and mixes a mark into the displayed image at the appropriate location, so that the position of the catheter is thereby identifiable.

17 Claims, 3 Drawing Sheets

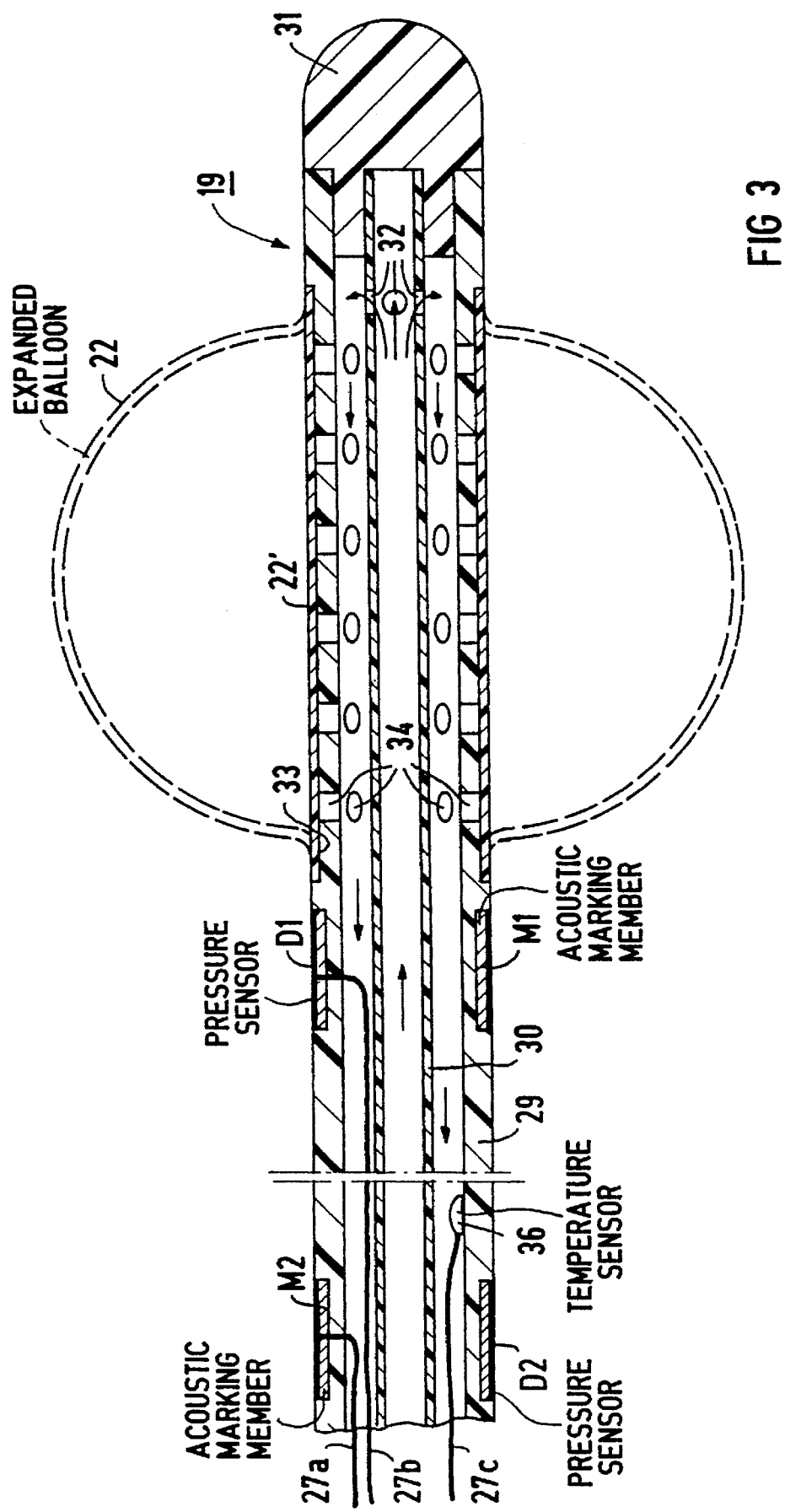

SYSTEM FOR THE TREATMENT OF PATHOLOGICAL TISSUE HAVING A CATHETER WITH A PRESSURE SENSOR

BACKGROUND OF THE INVENTION

1. Field of the Invention

The present invention is directed to a system for treatment of pathological tissue in a patient by charging a region containing the pathological tissue with heating radiation by means of a catheter.

2. Description of the Prior Art

It is known to treat pathological tissue by heating the pathological tissue, for example, with microwaves or ultrasound waves that are generated with suitable sources. To the extent that the resulting tissue temperatures lie below 45° C., the cell metabolism is disturbed with the consequence that growth is slowed in the case of tumors or a regression of the tumor even occurs. This type of treatment is known as local hyperthermia. When temperatures above 45° C. are reached, the cell protein coagulates, with the consequence that the tissue is necrotized. The latter type of treatment is referred to as thermotherapy.

In order to avoid the unintentional treatment of healthy tissue in the case of local hyperthermia and to avoid the unintentional necrotization of healthy tissue in the case of thermotherapy, suitable measures must be undertaken. In this context, U.S. Pat. No. 4,620,546 discloses that the region to be heated with a therapeutic ultrasound source be localized by detecting harmonics of the therapeutic ultrasound emitted by the therapeutic ultrasound source from the output signal of a diagnostic ultrasound transducer, and the position of the heated region identified on this basis is mixed into the ultrasound image. It is also known, for example from WO 91/13650, to bring a catheter into the region of the pathological tissue in a suitable way and to monitor the resulting temperatures with a temperature sensor integrated into the catheter. For protecting healthy tissue, moreover, the catheter can have a coolant flowing through it. Nonetheless, an unintentional treatment or necrotization of healthy tissue cannot be reliably precluded. In particular, the necrotization of healthy tissue can lead to a serious injury to the patient. In the treatment of benign prostate hyperplasia (BPH), for example, there is thus the risk of injury to one or both bladder sphincters. An injury to the outer sphincter (sphincter externus) leads to incontinence of the patient; injury to the inner sphincter (sphincter internus) deteriorates the procreative capability of the patient as a consequence of retrograde ejaculation.

A catheter is disclosed in U.S. Pat. No. 5,161,536 which is provided with an ultrasound transducer at its distal end. The ultrasound transducer responds to ultrasound incident thereon from an ultrasound diagnostic system, and generates output signals which are processed so that the position of the ultrasound transducer is mixed into the ultrasound image.

SUMMARY OF THE INVENTION

It is an object of the present invention to provide a therapy system for the treatment of pathological tissue in a patient by charging a region of the pathological tissue with heating radiation employing a catheter, wherein the risk of unintentional tissue damage, particularly necrotization of tissue, is minimized.

The above object is achieved in accordance with the principles of the present invention in a therapy apparatus for treating pathological tissue with heating radiation which includes a source of heating radiation having an effective therapeutic region, a catheter introducible into the body of a patient to be treated, the catheter having at least one pressure sensor in the region of its distal end, and an ultrasound locating system which generates an ultrasound image of a region to be treated, the ultrasound locating system including an ultrasound locating transducer and an image-generating unit to which the output signals of the pressure sensor are supplied. The output signals from the pressure sensor arise due to the charging of the pressure sensor with the diagnostic ultrasound waves emitted by the ultrasound locating transducer. The image-generating unit calculates the position of the pressure sensor in the ultrasound image on the basis of the output signals from the pressure sensor, and mixes a mark into the displayed image corresponding to and thus identifying, i.e. indicating, the position of the pressure sensor. The image-generating unit also identifies the position of the center of the region of therapeutic action, and mixes a further mark into the ultrasound image identifying, i.e. indicating, this center.

Before beginning a treatment, the catheter is introduced into the patient under diagnostic ultrasound supervision, using the ultrasound locating system, so that the pressure sensor comes to be located in the region of the tissue to which damage is to be avoided. The placement of the catheter can take place either by natural paths or by punctation, or endoscopically. The mark mixed into the ultrasound image by the image-generating unit identifies the tissue region to which damage is to be avoided. By observing this mark as well as the mark which identifies the position of the active therapeutic region, it is thus easily possible to select an alignment of the source of heating radiation and the subject to be treated relative to each other so that charging of the tissue region neighboring the pressure sensor with heating radiation is avoided. The risk of unintentional tissue damage, particularly necrotization of tissue, is thereby significantly reduced by the therapy apparatus of the invention.

In a preferred embodiment of the invention, displacement of the region to be treated can be undertaken dependent on the marks (or the signals generating the marks) which identify the position of the pressure sensor and/or the position of the region of therapeutic action. To this end, an adjustment unit can be provided for displacing the region to be treated and the region of therapeutic action of the heating radiation relative to each other, and a control unit for actuating this adjustment unit is also provided. The control unit is supplied with signals corresponding to the position of the pressure sensor from the image-generating unit, and the control unit actuates the adjustment unit so that charging of the tissue region neighboring the pressure sensor with heating radiation is suppressed. The therapy procedure is thus controlled by the control unit so that unintentional damage, particularly necrotization of the tissue region neighboring the pressure sensor, is virtually impossible. Additional reliability can be achieved in an embodiment wherein the source of heating radiation is a source of focused ultrasound waves, by supplying the control unit with the output signals of pressure sensor which arise due to the pressure sensor being charged with the focused ultrasound waves emanating from this source. The control unit can generate an alarm signal and/or suppress the output of ultrasound waves, or at least lower the intensity of the ultrasound waves, when the level of the output signal of the pressure sensor exceeds a limit value.

A further object of specifying a catheter that is especially suited for treatment of prostate conditions, for example of benign prostate hyperplasia or of prostate carcinoma, is achieved in an embodiment wherein the catheter is adapted for introduction into the urethra and has pressure sensors that are arranged at a distance from one another along the catheter, this distance corresponding to the distance between the sphincter externus and sphincter internus of the patient to be treated. Injury to the sphincters can thus be easily avoided, since these are exactly marked. The distance between the two sphincters can be easily identified in a known way from the ultrasound image.

In order to adapt the spacing of the pressure sensors to individual requirements, in a further version of the invention the distance between the pressure sensors is variable. There is also the possibility, however, of keeping a plurality of catheters on hand, each of which has a different spacing between the pressure sensors, whereby the spacing, for example, can be graduated in steps of 2 millimeters each.

In order to facilitate the positioning of the catheter, an expandable balloon is provided at the distal end of the catheter in a further version of the invention. This expandable balloon is disposed a distance from the pressure sensor neighboring it which is equal to the average distance of the inside of the urinary bladder from the sphincter internus. One then proceeds in the catheterization by first introducing the catheter with the balloon to such an extent that it is situated within the urinary bladder. Subsequently, the balloon is expanded and the catheter is withdrawn to such an extent that that side of the balloon facing away from the distal end of the catheter comes to be placed against the inside wall of the urinary bladder. The pressure sensor neighboring the distal end of the catheter is then located inside the sphincter internus, whereas the other pressure sensor is located inside the sphincter externus when the spacing of the pressure sensors from one another is correctly selected or set. The positioning of the catheter can be easily monitored in the ultrasound image.

In a further version of the invention, the catheter is provided with an acoustic marking member in the region of the pressure sensor (or in the region of at least one of the pressure sensors, in embodiments having more than one pressure sensor). The acoustic marking member has an acoustic impedance which deviates from the acoustic impedance of the surrounding tissue, so that it is easily identifiable in the ultrasound image. As a result, the positioning of the catheter under ultrasound supervision is further facilitated because the marking member is clearly perceptible in the ultrasound image, so that it is easily possible to determine the alignment of the catheter wherein the pressure sensor is located at the desired location. Additionally, by providing for further optical marking in the ultrasound image of the tissue region to be protected against damage, the risk of such damage is even further reduced.

In another embodiment of the invention the catheter has a coolant flowing through it during operation, so that injury to healthy tissue adjoining the catheter is practically precluded in the case of benign prostate hyperplasia of the urethra.

In a further embodiment of the invention the catheter has at least one temperature sensor in the region of its distal end, preferably between the pressure sensors, so that a qualitative acquisition of the temperature occurring in the region of the tissue to be treated is possible.

DESCRIPTION OF THE DRAWINGS

FIG. 3 is a longitudinal section through the distal end of the catheter of FIG. 2.

DESCRIPTION OF THE PREFERRED EMBODIMENTS

Figure 1:
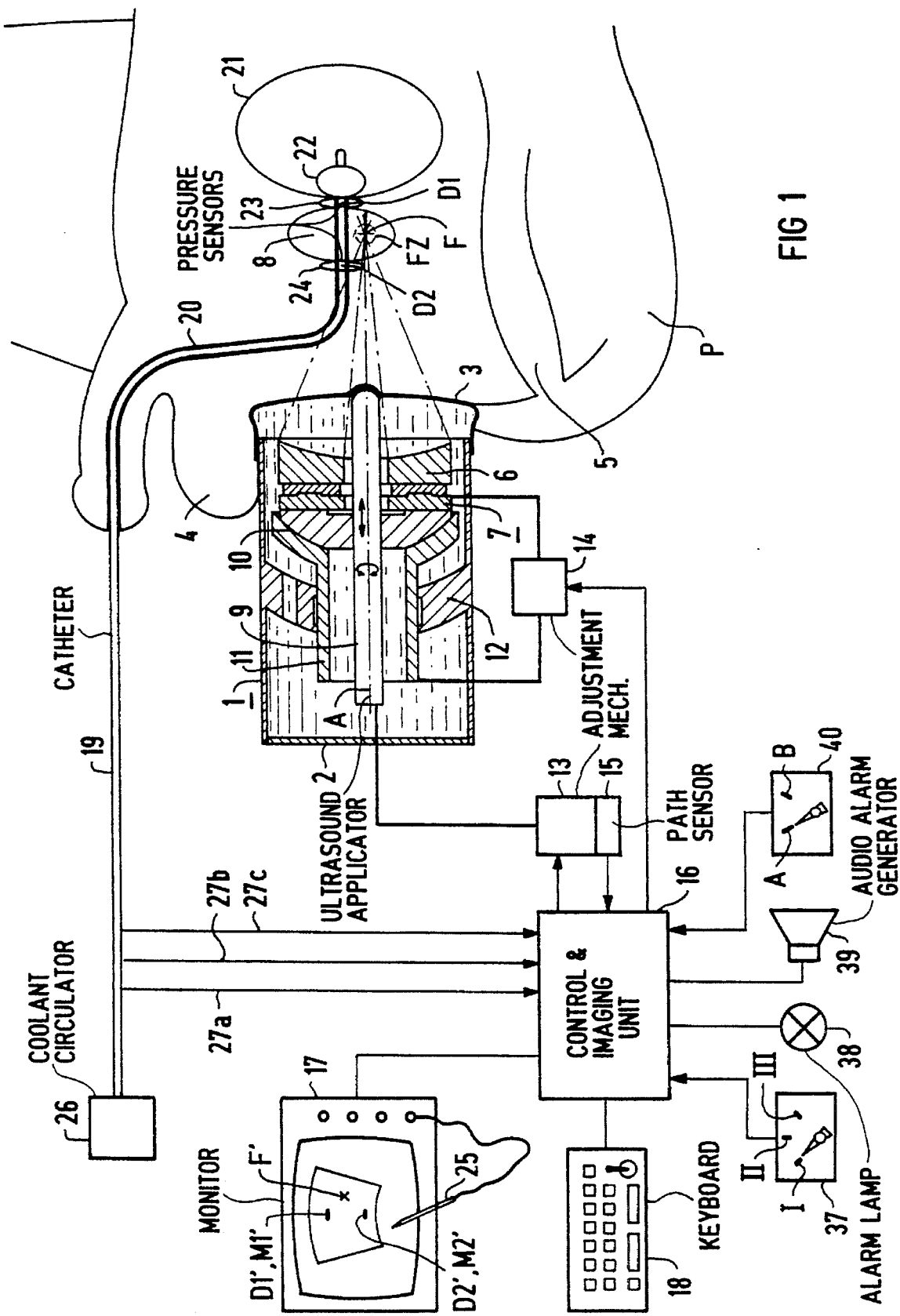
FIG. 1 is a schematic illustration of a longitudinal section through the body of a patient and a therapy system having a catheter constructed and operating in accordance with the principles of the present invention.

FIG. 1 shows the invention in the embodiment of a therapy system for treating benign prostate hyperplasia, which has a source of heating radiation, namely a therapeutic ultrasound applicator 1. The ultrasound applicator 1 has a tubular housing 2 that is filled with a liquid acoustic propagation medium, for example water, and has an application end closed with a flexible coupling membrane 3. The membrane 3 serves the purpose of coupling the ultrasound applicator 1 to the body surface of a patient to be treated. In the example of FIG. 1, the applicator 1 is acoustically coupled in the region of the perineum, i.e. between scrotum 4 and rectum 5 of the patient P. For acoustic coupling, the coupling membrane 3 of the ultrasound applicator 1 is pressed against the body surface of the patient P.

An ultrasound resonator 6 having an emission surface of a concave, spherically curved shape, is located in the inside of the housing 2. The ultrasound resonator 6 is attached to a carrying member composed of several parts that is generally referenced 7. The ultrasound resonator 6 is constructed in a known way, i.e. the ultrasound resonator 6 can be a single, appropriately shaped piezo ceramic member; the ultrasound transducer 6, however, can also be composed of a plurality of small piezo ceramic transducers arranged mosaically. In both instances, a backing (supporting member) having a suitable thickness can be provided in a known way that is not shown, this backing being formed of a material having a suitable acoustic impedance.

The ultrasound resonator 6 has an acoustic axis A along which the generated ultrasound waves propagate. The ultrasound waves converge in a focus F, which is the center of the spherically curved emission surface of the ultrasound resonator 6. A focus zone FZ that is indicated with broken lines in FIG. 1 surrounds the focus F. The focus zone FZ, which corresponds to the effective therapeutic region of the ultrasound waves, is that zone within which the peak pressure of the ultrasound waves is no lower than half the peak pressure maximally occurring in the focus zone FZ (−6 dB zone). The drive of the ultrasound resonator 6 ensues with an electric generator contained in a control and imaging unit which is described below.

An ultrasound locating transducer 9, preferably a B-scan applicator, is accepted in a bore of the carrying member 7, this ultrasound locating transducer 9 serving the purpose of locating the region to be treated, i.e. the prostate 8. In order to be able to align the ultrasound locating transducer 9 relative to the prostate 8 such that a good image is obtained, the ultrasound locating transducer 9 is accepted longitudinally displaceable and rotatable in the bore of the carrying member 7, this being indicated in FIG. 1 by corresponding arrows. During operation of the ultrasound locating transducer 9, it lies against the body surface of the patient P with the coupling membrane 3 therebetween for a good image quality.

As may be seen from FIG. 1, the side of the carrying member 7 facing away from the ultrasound resonator has a spherically curved bearing surface 10 that cooperates with a spherically cap-shaped bearing surface of a corresponding radius in a bearing member 11, that is accepted longitudinally displaceable but non-rotatably in the bore of a housing flange 12. The center of the bearing surface 10 is different from the focus F. It is thus possible to spatially modify the alignment of the ultrasound resonator 6 and of the ultrasound locating transducer 9 relative to the body of the patient P without a relative motion occurring between the coupling membrane 3 and the body surface of the patient P.

Adjustment units 13 and 14 are provided for adjusting the ultrasound locating transducer 9 relative to the carrying member 7 and for adjusting the carrying member 7 having the ultrasound resonator 6 relative to the housing 2 and relative to the coupling membrane 3. This latter adjustment possibility serves the purpose of displacing the focus zone FZ and the patient relative to one another. The adjustment unit 13 and 14 are schematically indicated in FIG. 1 and are preferably motor-driven adjustment units. A position sensor 15 schematically indicated in FIG. 1 is allocated to the adjustment unit 13. This position sensor 15 provides signals corresponding to the momentary position of the ultrasound locating transducer 9 relative to the carrying member 7. Both the adjustment units 13 and 14 and the position sensor 15 are connected to a control and imaging unit 16 to which a monitor 17 and a keyboard 18 are connected. The control and imaging unit 16 cooperates with the ultrasound locating transducer 9 in a known way as an imaging diagnostics installation for generating image information, namely ultrasound B-images, with the current ultrasound image being displayed on the monitor 17. The arrangement of the ultrasound locating transducer 9 relative to the ultrasound resonator 6 is selected such that the acoustic axis A of the ultrasound resonator 6 lies in the body slice of the patient P shown in the ultrasound B-image. Taking the output signal of the position sensor 15 into consideration, the control and imaging unit 16 mixes a mark F' into the ultrasound image, this mark F' identifying the current position of the center of the focus zone FZ (i.e., the center of the therapeutic action).

In addition to containing the image-generating electronics required for producing ultrasound images, the control and imaging unit 16 contains all circuits that are required for driving the adjustment units 13 and 14 as well as for driving the ultrasound resonator 6.

FIG. 1 also shows a catheter 19 that is introduced into the urethra 20 of the patient P for the implementation of a treatment, such that the distal end of the catheter 19 projects into the urinary bladder 21. The catheter 19 has an expandable balloon 22 at its distal end. When the distal end of the catheter 19 is advanced into the urinary bladder 21, the balloon 22 is inflated. Subsequently, the catheter is retracted such that the balloon 22 presses against the region of the inside wall of the urinary bladder 21 surrounding the opening of the urethra 21. The region of the distal end of the catheter 19, namely between the balloon 22 and the proximal end, is provided with two pressure sensors D1 and D2. The pressure sensors D1 and D2 have a spacing from one another that essentially corresponds to the distance between the sphincter internus 23 and the sphincter externus 24 of the patient P to be treated, whereby the distance between the pressure sensor D1 and the side of the balloon 22 facing it has a spacing that identically corresponds to the spacing of the inside of the urinary bladder 21 from the sphincter internus that is averaged over the patient population. The pressure sensors D1 and D2 are preferably annular and are constructed using piezoelectrically activated polymer foil, for example polyvinylidenefluoride (PVDF) foil, which is metallized in a known manner to form electrodes for the purpose of electrical contacting.

The output signals of the pressure sensors D1 and D2 are supplied to the control and imaging unit 16 via lines 27a and 27b. The control and imaging unit 16 undertakes a comparison, against a limit value, of at least those output signals of the pressure sensors D1 and D2 which arise due to ultrasound waves, emanating from the ultrasound resonator 6 during treatment, being incident on the pressure sensors D1 and D2. The limit value is dimension so that injury to the bladder sphincters is precluded as long as the amplitude of the ultrasound waves which are present in the region of the pressure sensors D1 and D2 is not so high that the output signal of the pressure sensors exceeds the limit value. The reaction of the therapy apparatus to an upward transgression of the limit value is dependent on which of three possible operating modes is selected by a switch 37.

In the operating mode corresponding to the switch position referenced I, the control and imaging unit 16 causes a humanly perceptible alarm to be generated, such as by driving a warning lamp 38 and/or an acoustic signal generator 39. Alternatively or additionally, an optical alarm signal may be generated on the monitor 17, for example by causing the monitor image to flash when the limit value is upwardly transgressed.

In the operating mode corresponding to the switch position referenced II, the amplitude of the generated ultrasound waves is reduced, given an upward transgression of the limit value, to such an extent that the output signal of the pressure sensors D1 and D2 falls below the limit value.

In the operating mode corresponding to switch position III, the control and imaging unit 16 entirely suppresses the emission of ultrasound waves given an upward transgression of the limit value.

In operating mode II as well as in operating mode III, the generation of alarm signals can additionally ensue in the manner set forth in conjunction with operating mode I.

A switch 40 is connected to the control and imaging unit 16 in addition to the switch 37, the switch 40 having two switch positions referenced A and B. When the switch 40 is in switch position A, the control and imaging unit 16 evaluates the output signals of the pressure sensors D1 and D2 not only during operation of the ultrasound resonator 6, but also during operation of the ultrasound locating transducer 9. The control and imaging unit 16 calculates the points in time at which those output signals of the pressure sensors D1 and D2 appear which arise by virtue of the diagnostic ultrasound generated by the ultrasound locating transducer 9 being incident on the pressure sensors D1 and D2. A defined picture element, or a defined image zone, in the current ultrasound image corresponds to each points in time. Marks referenced D1' and D2' in FIG. 1 are mixed into the image at the appropriate locations shown on the monitor 17. Further, the control and imaging unit 16, utilizing the signal of the path sensor 15, calculates the position of the pressure sensors D1 and D2 relative to the focus zone FZ.

When the switch 40 assumes the position referenced B, the consideration of the output signals of the pressure sensors D1 and D2 ensues only during operation of the locating transducer 9, but not during operation of the ultrasound resonator 6.

For implementing a treatment, one proceeds by applying the coupling membrane of the ultrasound applicator 1 to the perineum of the patient P to be respectively treated, who preferably assumes what is referred to as the lithotomy position (see Pschyrembel, "Klinisches Woerterbuch", Edition 185–250, page 1156). The coupling ensues so that no air bubbles are enclosed between the body surface and the coupling membrane 3. Thereupon, the production of ultrasound images is started by appropriate actuation of the keyboard 18. Likewise by appropriate actuation of the keyboard, the adjustment units 13 and 14 are now actuated such that an alignment of the ultrasound locating transducer 9 relative to the body of the patient P is obtained wherein the prostate 8 is clearly imaged in the ultrasound image. The distance between the two sphincters is now identified and displayed on the monitor 17 by the control and imaging unit 16 in a known way, for example by marking the sphincter internus 23 and the sphincter externus 24 in the ultrasound image with a light pen 25. Subsequently, a catheter 19 whose pressure sensors D1 and D2 have a spacing from one another that essentially corresponds to the spacing between the two bladder sphincters of the patient to be treated, is selected from a stock of catheters 19 whose respective pressure sensors D1 and D2 have different spacings from one another. This catheter 19 is now introduced into the urethra 20 of the patient P and is positioned with the assistance of the balloon 22 such that the pressure sensors D1 and D2 are located in the region of tissue that is not to be heated, i.e. inside the sphincter internus 23 and, respectively, the sphincter externus 24.

A region of the prostate 8 to be treated can now be marked in the ultrasound image with the light pen 25 or with a similar input means. In response to an appropriate actuation of the keyboard 18, the control and imaging unit 16 now actuates the adjustment unit 14 such that the focus zone FZ is displaced into that region of the prostate 8 that corresponds to the region marked with the light pen 25. This is shown in the ultrasound image in that the mark F' comes into coincidence with the region marked with the light pen 25 after the actuation of the adjustment unit 14 has been carried out. When this is the case, the control and imaging unit 19 drives the ultrasound resonator 6 to generate ultrasound. Continuous sound is emitted over a time span that is selected such that the temperature required for the necrotization of tissue, which usually lies beyond 45° C., is exceeded.

Thereupon, a region of the prostate 8 to be treated can again be marked with the light pen 25 and can be treated in the described way. The risk that the sphincter internus 23 or, respectively, sphincter externus 24 will be injured or destroyed in this procedure, with the consequence of a deterioration of the procreative ability or, respectively, of incontinence, is less than slight, since the two bladder sphincters have their position clearly identified in the ultrasound image by the clearly perceptible images D1' and D2' of the pressure sensors D1 and D2.

It is thus substantially impossible to mistakenly mark a region to be treated with a light pen 25 that lies entirely or partially within one of the sphincters. When the switch 40 assumes the position referenced A, either the attending personnel are also alerted (operating mode I), the amplitude of the ultrasound waves is lowered to harmless values (operating mode II) or the emission of ultrasound waves is entirely suppressed (operating mode III) as soon as the intensity of the ultrasound waves in the region of the pressure sensors D1 and D2, and thus in the region of the bladder sphincters, upwardly exceeds the allowable limit value.

Moreover, there is also the possibility of tracing the contours of a region of the prostate 8 to be treated with the light pen 25 in the ultrasound image. In response to an appropriate actuation of the keyboard 18, the focus zone FZ is then displaced step-by-step within the region traced with the light pen 25 upon activation of the ultrasound resonator 6 such that the entire traced region is charged with ultrasound waves and is necrotized. Here, too, the risk that a region of treatment marked with the light pen 25 that mistakenly contains one or both bladder sphincters is inconceivably slight. Even if this were to occur, injury would not be possible with the switch 40 in the position referenced A since, dependent on whether the switch 37 is in position I, II or III, either the attending personnel will be alerted, or the amplitude of the ultrasound waves will be lowered, or the emission of ultrasound waves will be completely suppressed.

In any case, regardless of the operating mode selected by means of the switches 37 and 40, the control and imaging unit 16 calculates the positions of the pressure sensors D1 and D2 relative to the focus zone FZ in the manner described above, and drives the adjustment unit 14 so that displacement of the focus zone FZ into the current position of the pressure sensor D1 or D2 is precluded. Even under the worst conditions, it is assured with extremely high probability that injury to the bladder sphincters will be avoided.

In order to preclude damage to the urethra 20, it is provided that a coolant flows through the catheter 19. The corresponding coolant circulator 26 is shown in FIG. 1, which also serves as a heat exchanger. In order to be able to monitor the therapy process, at least one temperature sensor is arranged in the region of the distal end of the catheter 19 between the pressure sensors D1 and D2. The output signals supplied by these sensors are supplied to the control and imaging unit 16, this being illustrated in FIG. 1 by schematically indicated line 27c. The evaluation of the output signals of the sensors is assumed by the control and imaging unit 16 which also mixes the measured pressure and temperature values into the ultrasound image. Further details regarding the cooling and the arrangement of the sensors shall be set forth in conjunction with FIG. 3.

Figure 2:
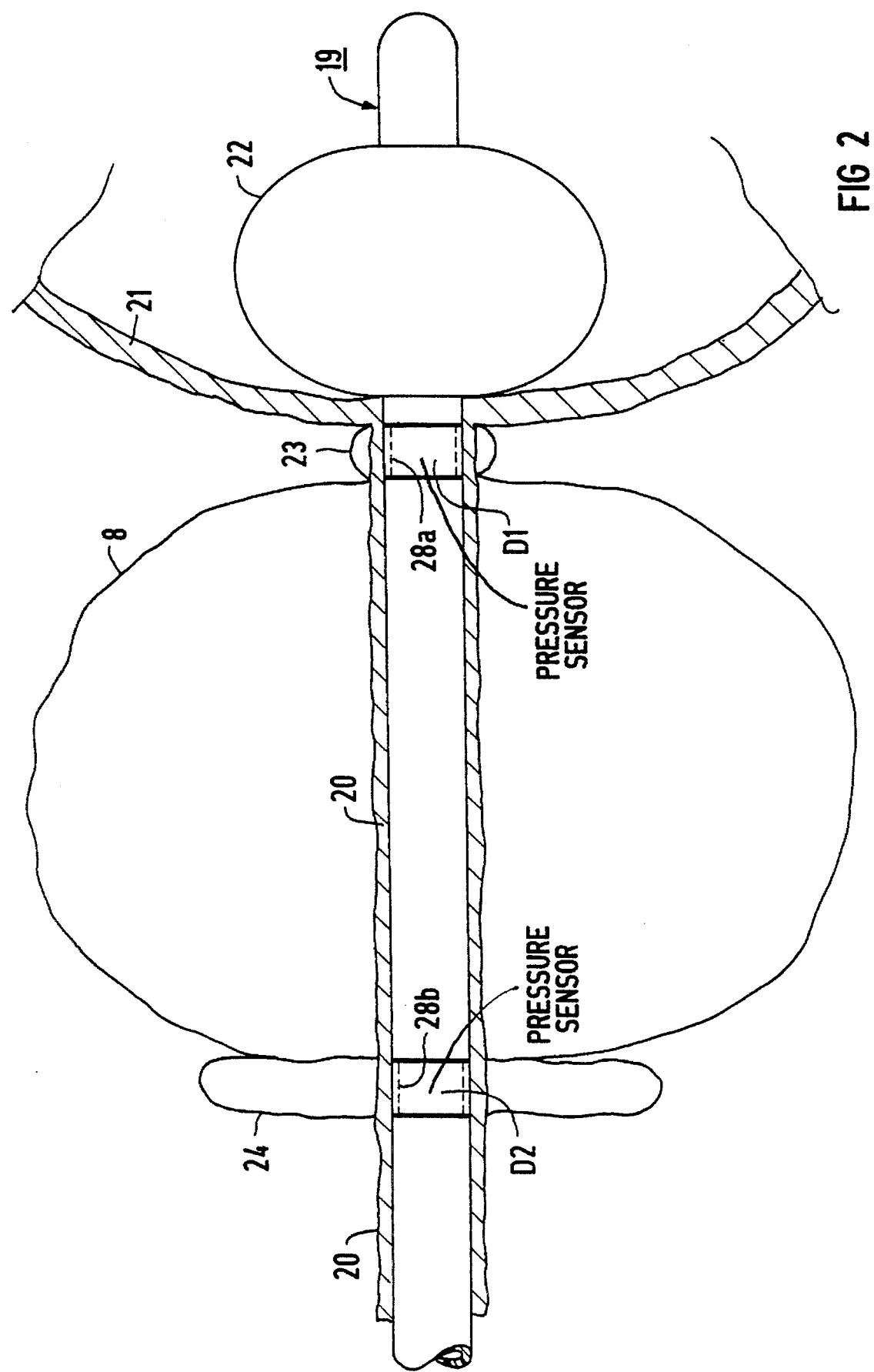
FIG. 2 is an enlarged, schematic illustration of the distal end of the catheter of FIG. 1 introduced into the body of the patient together with the surrounding organs.

In FIG. 2, wherein only the urethra 20 and the prostate 8 are shaded for clarity, the distal end of the catheter 19 correctly placed in the urethra 20 is shown. The catheter 19 optimally corresponds to the anatomy of the patient P to be treated, since the spacing of the pressure sensors D1 and D2 from each other is identical to the spacing between the sphincter internus 23 and sphincter externus 24. As also shown in FIG. 2, the annular pressure sensors D1 and D2 are accepted in respective channels 28a and 28b.

The structure of the catheter 19 in the region of its distal end may be seen in detail in FIG. 3. The catheter 19 is biluminar, having a flexible, outer catheter tube 29 in which an inner catheter tube 30 that is likewise flexible is coaxially arranged. A closure part 31 formed by a rounded-off introduction end is provided at the distal end; this closure part 31 closes the outer catheter tube 29 liquid-tight. The inner catheter tube 30 is accepted liquid-tight in a bore of the closure part 31. Just before the closure part 31, the inner catheter tube 30 has a plurality of flow-through openings 32 that produce a connection between the inner lumen surrounded by the inner catheter tube 30 and the outer lumen situated between the outer catheter tube 29 and the inner catheter tube 30. A preferably liquid coolant can be caused to flow through the catheter 19 with the coolant circulator 26 in the way indicated by the arrows in FIG. 3.

The catheter 19 shown in FIG. 3 differs from the embodiment shown in FIGS. 1 and 2 by virtue of the pressure sensors D1 and D2 not being directly accepted into the channels 28a and 28b of the outer catheter tube 29, but instead being attached on annular, acoustic marking members M1 and M2. The acoustic marking members M1 and M2 are accepted in the channels 28a and 28b of the outer catheter tube 29, together with the pressure sensors D1 and D2. The marking members MI and M2 are composed of a material, for example, stainless steel, having an acoustic impedance which deviates from that of the surrounding tissue. The marking members M1 and M2 can thus be clearly perceived in the ultrasound images generated by the ultrasound locating transducer 9 and the control and imaging unit 16. Images M1' and M2' of the marking members M1 and M2 appear in the ultrasound image at the same location as the marks D1' and D2', as indicated by the additional entry of the references M1' and M2' in FIG. 1. When the acoustic marking members M1 and M2 are present according to the embodiment of FIG. 3, the monitoring of the output signals of the pressure sensors D1 and D2 during the operation of the ultrasound locating transducer 9 can be suppressed, since the positions of the pressure sensors D1 and D2 are indicated in the ultrasound image by the marks M1' and M2' of the marking members M1 and M2. The positions of the marking members M1 and M2 relative to the focus zone FZ can also be calculated by the control and imaging unit 16 on the basis of known image processing methods, and taking the output signals of the path sensor 15, proceeding from the positions of the images M1' and M2' in the ultrasound image, into consideration.

A channel 33 that accepts a flexible balloon part 22' is introduced into the outer generated surface of the outer catheter tube 29 between the closure part 31 and the pressure sensor M1. This flexible balloon part 22' has the region of its two ends connected liquid-tight to the outer catheter tube 29, for example by gluing. As long as the pressure of the coolant flowing through the catheter 19 does not exceed a limit value, the balloon part 22' has the shape shown with solid lines in FIG. 3 wherein it presses against the channel 33. Since a plurality of openings 34 penetrating the wall of the outer catheter tube 29 are provided in the region of the channel 33, however, there is the possibility of expanding the balloon part 22' into the balloon 22 by increasing the pressure of the coolant in the way indicated with broken lines in FIG. 3.

A temperature sensor 36 is applied to the inside wall of the outer catheter tube 29 at that side of the marking member M1 facing away from the balloon 22; this sensor is in communication with the control and imaging unit 16 via the schematically indicated line 27c.

Silicone rubber or polyethylene, for example, are suitable as materials for the inner catheter tube 29, for the outer catheter tube 30 and for the closure part 31.

The above-described exemplar,/embodiment is directed to the treatment of benign prostate hyperplasia. However, other maladies can also be treated. If tumor conditions are to be treated, the regions to be treated are only heated to such an extent that a disturbance of the cell metabolism ensues but the coagulation of the cell protein is suppressed.

As noted above, the output signals of the pressure sensors D1 and D2 can be monitored both during the operation of the ultrasound resonator 6 and the operation of the ultrasound locating transducer 9, thereby avoiding unintentional injury to the bladder sphincters with especially high reliability. Generally, however, it will be sufficient to undertake monitoring of the output signals of the pressure sensors D1 and/or D2 either only during operation of the ultrasound resonator 6 or only during operation of the ultrasound locating transducer 9. It is clear that the desired therapeutic effect need not necessarily be achieved using ultrasound waves as the heating radiation if evaluation of the output signals of the pressure sensors D1 and D2 ensues only during operation of the ultrasound locating transducer 9. This permits the use of other types of heating radiation, for example, microwaves.

The generation of the ultrasound waves need not necessarily ensue using a piezoelectric ultrasound resonator. It is also possible to employ ultrasound transducers operating according to other principles, for example magnetostrictively. The focusing of the ultrasound waves also need not necessarily ensue on the basis of an appropriate shaping of the emission face of the ultrasound resonator. Alternatively, acoustic lenses and/or reflectors can be employed for focusing.

Instead of a mark F' which identifies the center of the region of therapeutic action, a mark can alternatively be employed which indicates the contour of the region of therapeutic action, and which may also indicate the center thereof.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus for treating pathological tissue with heating radiation comprising:

a source of heating radiation, said heating radiation having an active therapeutic region with a center;

a catheter introducible into the body of a patient to be treated with said heating radiation, said catheter having a distal end and a pressure sensor disposed approximately at said distal end, said pressure sensor generating output signals corresponding to a pressure sensed by said pressure sensor; and ultrasound locating means for generating an ultrasound image of a region to be treated by said heating radiation, said ultrasound locating means including an ultrasound locating transducer which emits diagnostic ultrasound waves and an image-generating unit to which said output signals of said pressure sensor are supplied, said output signals arising due to charging of said pressure sensor with said diagnostic ultrasound waves, and said image-generating unit including means for identifying a position of said pressure sensor in said ultrasound image on the basis of said output signals, and for mixing a mark into said ultrasound image identifying the position of said pressure sensor, and for mixing a further mark into said ultrasound image identifying a position of the center of said active therapeutic region.

2. A therapy apparatus for treating pathological tissue with heating radiation comprising:

a source of focused ultrasound therapy waves having an active therapeutic region;

a catheter introducible into the body of a patient to be treated with said focused ultrasound therapy waves, said catheter having a distal end and a pressure sensor disposed approximately at said distal end, said pressure sensor generating output signals corresponding to a pressure sensed by said pressure sensor arising due to charging of said pressure sensor with said focused ultrasound therapy waves; and ultrasound locating means for generating an ultrasound image of a region to be treated by said focused ultrasound therapy waves, said ultrasound locating means including an ultrasound locating transducer which emits diagnostic ultrasound waves and an image-generating unit to which said output signals of said pressure sensor are supplied, said pressure sensor also generating output signals arising due to charging of said pressure sensor with said diagnostic ultrasound waves, said image-generating unit including alarm means for initiating a reaction if said output signal has a level which upwardly exceeds a limit value, and said image-generating unit including means for identifying the position of said pressure sensor in said ultrasound image on a basis of said output signals, and for mixing a mark into said ultrasound image identifying a position of said pressure sensor, and for mixing a further mark into said ultrasound image identifying the position of said active therapeutic region.

3. A therapy apparatus as claimed in claim 2 wherein said means for initiating a reaction comprises means for generating a humanly perceptible alarm signal.

4. A therapy apparatus as claimed in claim 2 wherein said means for initiating a reaction comprises means for suppressing output of said focused ultrasound therapy waves from said source of focused ultrasound therapy waves.

5. A therapy apparatus as claimed in claim 2 wherein said focused ultrasound therapy waves have an intensity, and wherein said means for initiating a reaction comprise means for lowering said intensity of said focused ultrasound therapy waves.

6. A therapy apparatus as claimed in claim 2 further comprising means for circulating a coolant through said catheter.

7. A therapy apparatus as claimed in claim 2 further comprising a temperature sensor disposed approximately at said distal end of said catheter.

8. A therapy apparatus for treating pathological tissue with heating radiation comprising:
   a source of heating radiation, said heating radiation having an active therapeutic region;
   a catheter adapted for introduction into the urethra of a patient to be treated with said heating radiation, said catheter having a distal end and having a first and second a pressure sensors disposed approximately at said distal end, said first and said second pressure sensors being disposed a distance from each other along said catheter, said distance adapted to correspond to the distance between the sphincter externus and the sphincter internus of said patient to be treated, said first and said second pressure sensors each generating output signals corresponding to pressure respectively sensed by said first and second pressure sensors; and
   ultrasound locating means for generating an ultrasound image of a region to be treated by said heating radiation, said ultrasound locating means including an ultrasound locating transducer which emits diagnostic ultrasound waves and an image-generating unit to which said output signals of said first and said second pressure sensor are supplied, said output signals arising due to charging of said first and second pressure sensors with said diagnostic ultrasound waves, and said image-generating unit including means for identifying a position of said first and said second pressure sensors in said ultrasound image on the basis of said output signals, and for mixing respective marks into said ultrasound image identifying the positions of said first and said second pressure sensors, and for mixing a further mark into said ultrasound image identifying a position of said active therapeutic region.

9. A therapy apparatus for treating pathological tissue with heating radiation comprising:
   a source of heating radiation, said heating radiation having an active therapeutic region;
   a catheter adapted for introduction into the urethra of a patient to be treated with said heating radiation, said catheter having a distal end and a pressure sensor disposed approximately at said distal end, said pressure sensor generating output signals corresponding to a pressure sensed by said pressure sensor;
   ultrasound locating means for generating an ultrasound image of a region to be treated by said heating radiation, said ultrasound locating means including an ultrasound locating transducer which emits diagnostic ultrasound waves and an image-generating unit to which said output signals of said pressure sensor are supplied, said output signals arising due to charging of said pressure sensor with said ultrasound diagnostic waves, and said image-generating unit including means for identifying a position of said pressure sensor in said ultrasound image on the basis of said output signals, and for mixing a mark into said ultrasound image identifying the position of said pressure sensor, and for mixing a further mark into said ultrasound image identifying a position of said active therapeutic region; and
   an expandable balloon disposed at said distal end of said catheter spaced from said pressure sensor by a distance adapted to correspond to an average spacing of the inside of the bladder from the sphincter externus of a population of patients to be treated.

10. A therapy apparatus for treating pathological tissue with heating radiation comprising:
   a source of heating radiation, said heating radiation having an active therapeutic region;
   a catheter introducible into the body of a patient to be treated with said heating radiation, said catheter having a distal end and a pressure sensor disposed approximately at said distal end, said pressure sensor generating output signals corresponding to a pressure sensed by said pressure sensor;
   ultrasound locating means for generating an ultrasound image of a region to be treated by said heating radiation, said ultrasound locating means including an ultrasound locating transducer which emits diagnostic ultrasound waves and an image-generating unit to which said output signals of said pressure sensor are supplied, said output signals arising due to charging of said pressure sensor with said diagnostic ultrasound waves, and said image-generating unit including means for identifying a position of said pressure sensor in said ultrasound image on the basis of said output signals, and for mixing a mark into said ultrasound image identifying the position of said pressure sensor, and for mixing a further mark into said ultrasound image identifying a position of said active therapeutic region; and
   an acoustic marking member disposed on said catheter in a region of said pressure sensor, said acoustic marking member having an acoustic impedance adapted to deviate from the acoustic impedance of surrounding tissue when said catheter is introduced into said patient so that said marking member appears in said image generated by said ultrasound image-generating unit.

11. A therapy apparatus for treating pathological tissue with heating radiation comprising:
   a source of heating radiation said heating radiation having an active therapeutic region;

a catheter introducible into the body of a patient to be treated with said heating radiation, said catheter having a distal end and two pressure sensors spaced from each other along said catheter approximately at said distal end, said pressure sensors each generating output signals corresponding to pressure respectively sensed by said pressure sensors;

ultrasound locating means for generating an ultrasound image of a region to be treated by said heating radiation, said ultrasound locating means including an ultrasound locating transducer which emits diagnostic ultrasound waves and an image-generating unit to which said output signals of said two pressure sensors are supplied, said output signals arising due to charging of each of said two pressure sensors with said diagnostic ultrasound waves, and said image-generating unit including means for identifying the respective positions of said two pressure sensors in said ultrasound image on the basis of said output signals and for mixing respective marks into said ultrasound image identifying the positions of said two pressure sensors, and for mixing a further mark into said ultrasound image identifying a position of said active therapeutic region; and a temperature sensor disposed on said catheter between said two pressure sensors.

12. A therapy apparatus for treatment of pathological tissue in a patient with heating radiation comprising:

a source of heating radiation, said heating radiation having an active therapeutic region;

a catheter introducible into the body of a patient to be treated, said catheter having a distal end with a pressure sensor disposed approximately at said distal end, said pressure sensor generating output signals arising due to charging of said pressure sensor with pressure;

ultrasound locating means for generating an ultrasound image of a region of said patient to be treated, including an ultrasound locating transducer which generates diagnostic ultrasound waves and an image generating means, supplied with said output signals from said pressure sensor which arise due to charging of said pressure sensor with said diagnostic ultrasound waves, for identifying a position of said pressure sensor in said ultrasound image on the basis of said output signals of said pressure sensor; and adjustment means for producing relative displacement between said region to be treated and said active therapeutic region, including control means, supplied with said output signals of said pressure sensor, for actuating said adjustment means for avoiding charging of tissue in a region surrounding said pressure sensor with said heating radiation.

13. A therapy apparatus as claimed in claim 12 wherein said image-generating means includes means for identifying a position of said pressure sensor in said ultrasound image by mixing a mark into said ultrasound image at a location corresponding to the position of said pressure sensor.

14. A therapy apparatus as claimed in claim 12 wherein said source of heating radiation comprises a source of focused ultrasound therapy waves, wherein said pressure sensor generates output signals arising due to charging of said pressure sensor with said focused ultrasound therapy waves, said output signal being supplied to said image-generating means and said image-generating means including alarm means for initiating a reaction if said output signals have a level which upwardly exceeds a limit value.

15. A therapy apparatus as claimed in claim 14 wherein said means for initiating a reaction comprises means for generating a humanly perceptible alarm signal.

16. A therapy apparatus as claimed in claim 14 wherein said means for initiating a reaction comprises means for suppressing output of said focused ultrasound therapy waves from said source of focused ultrasound therapy waves.

17. A therapy apparatus as claimed in claim 14 wherein said focused ultrasound therapy waves have an intensity, and wherein said means for initiating a reaction comprise means for lowering said intensity of said focused ultrasound therapy waves.

* * * * *